United States Patent
Jang et al.

(10) Patent No.: US 10,418,656 B2
(45) Date of Patent: Sep. 17, 2019

(54) COMPOUND COMPRISING AROMATIC RING HAVING SULFONAMIDE AND ION TRANSPORT GROUP, POLYMER COMPRISING SAME, AND POLYELECTROLYTE MEMBRANE USING SAME

(71) Applicant: LG CHEM, LTD., Seoul (KR)

(72) Inventors: Yong Jin Jang, Daejeon (KR); Joong Jin Han, Daejeon (KR); Youngjea Kim, Daejeon (KR); Esder Kang, Daejeon (KR); Sehee Jung, Daejeon (KR); Hyun Woog Ryu, Daejeon (KR); Yunah Yu, Daejeon (KR)

(73) Assignee: LG CHEM, LTD., Seoul (KR)

( * ) Notice: Subject to any disclaimer, the term of this patent is extended or adjusted under 35 U.S.C. 154(b) by 136 days.

(21) Appl. No.: 15/542,747

(22) PCT Filed: Jan. 26, 2016

(86) PCT No.: PCT/KR2016/000834
§ 371 (c)(1),
(2) Date: Jul. 11, 2017

(87) PCT Pub. No.: WO2016/122195
PCT Pub. Date: Aug. 4, 2016

(65) Prior Publication Data
US 2018/0006320 A1    Jan. 4, 2018

(30) Foreign Application Priority Data
Jan. 26, 2015 (KR) .................. 10-2015-0011994

(51) Int. Cl.
*H01M 8/1027* (2016.01)
*C07C 311/48* (2006.01)
(Continued)

(52) U.S. Cl.
CPC .......... *H01M 8/1027* (2013.01); *B01J 39/19* (2017.01); *B01J 47/12* (2013.01); *C07C 311/48* (2013.01);
(Continued)

(58) Field of Classification Search
CPC ........ H01M 8/1027; H01M 8/00; H01M 8/10; H01M 8/1004; H01M 8/18; H01M 8/188;
(Continued)

(56) References Cited

U.S. PATENT DOCUMENTS

| 8,853,448 B2 | 10/2014 | Sanchez et al. |
| 2003/0013817 A1* | 1/2003 | Lu ........................ B01D 69/141 525/328.4 |

(Continued)

FOREIGN PATENT DOCUMENTS

| JP | 2011040363 A | * | 2/2011 |
| JP | 2011140605 A | * | 7/2011 |

(Continued)

OTHER PUBLICATIONS

Extended European Search Report dated Jul. 18, 2018 for Application No. 16743673.2.

(Continued)

*Primary Examiner* — Sean P Cullen
(74) *Attorney, Agent, or Firm* — Birch, Stewart, Kolasch & Birch, LLP

(57) ABSTRACT

The present specification relates to a compound comprising an aromatic ring, a polymer comprising the same, a polyelectrolyte membrane comprising the same, a membrane-electrode assembly comprising the polyelectrolyte membrane, a fuel cell comprising the membrane-electrode assembly, and a redox flow battery comprising the polyelectrolyte membrane.

17 Claims, 3 Drawing Sheets

(51) Int. Cl.
| | |
|---|---|
| *C07C 321/28* | (2006.01) |
| *B01J 39/19* | (2017.01) |
| *B01J 47/12* | (2017.01) |
| *C07C 317/14* | (2006.01) |
| *C08G 65/40* | (2006.01) |
| *C08J 5/22* | (2006.01) |
| *H01M 8/1004* | (2016.01) |
| *H01M 8/241* | (2016.01) |
| *C08G 65/00* | (2006.01) |
| *H01M 8/1067* | (2016.01) |
| *H01M 8/18* | (2006.01) |
| *H01M 8/1018* | (2016.01) |

(52) U.S. Cl.
CPC .......... *C07C 317/14* (2013.01); *C07C 321/28* (2013.01); *C08G 65/00* (2013.01); *C08G 65/4012* (2013.01); *C08J 5/2262* (2013.01); *H01M 8/1004* (2013.01); *H01M 8/1067* (2013.01); *H01M 8/241* (2013.01); *C08G 2650/64* (2013.01); *C08J 2371/10* (2013.01); *H01M 8/188* (2013.01); *H01M 2008/1095* (2013.01); *Y02E 60/528* (2013.01)

(58) Field of Classification Search
CPC .......... H01M 8/241; B01J 39/19; B01J 47/12; C07C 311/48; C07C 317/14; C07C 321/28; C08G 65/00; C08G 65/4012; C08J 5/2262
USPC .................. 429/465, 492, 493, 494; 521/25; 570/127, 129, 184, 185
See application file for complete search history.

(56) References Cited

U.S. PATENT DOCUMENTS

| | | | |
|---|---|---|---|
| 2005/0118513 A1* | 6/2005 | Ugawa | H01M 10/0567 429/339 |
| 2009/0163692 A1 | 6/2009 | Moore et al. | |
| 2009/0269644 A1 | 10/2009 | Hamrock et al. | |
| 2012/0302725 A1 | 11/2012 | Teasley | |
| 2014/0065512 A1 | 3/2014 | Kwon et al. | |
| 2015/0328630 A1 | 11/2015 | Yoo et al. | |

FOREIGN PATENT DOCUMENTS

| | | |
|---|---|---|
| JP | 2011-181423 A | 9/2011 |
| JP | 2013-515846 A | 5/2013 |
| JP | 2013-218868 A | 10/2013 |
| JP | 2014-520082 A | 8/2014 |
| KR | 10-2003-0076057 A | 9/2003 |
| KR | 10-2013-0062252 A | 6/2013 |
| WO | WO 2014/200286 A2 | 12/2014 |

OTHER PUBLICATIONS

Hamrock et al., "New Proton Exchange Membrane Development at 3M," Proceedings published by the American Chemical Society, 2011, 1 page.

Xu et al., "Highly Conductive Aromatic Ionomers with Perfluorosulfonic Acid Side Chains for Elevated Temperature Fuel Cells," Macromolecules, vol. 44, Jun. 7, 2011, pp. 4605-4609.

Giam et al., "Evaluation of Ground-State Electronic Energy from Fluorine Nuclear Magnetic Resonance Shielding. I. Prediction of Enthalpies of Reaction for Formation of Lewis Acid Adducts of Benzophenones", Journal of the American Chemical Society, vol. 89, No. 10, May 10, 1967, pp. 2397-2401.

International Search Report for PCT/KR2016/000834 dated Apr. 1, 2016.

Toulgoat et al., "Efficient Preparation of New Fluorinated Lithium and Ammonium Sulfonimides", J. Org. Chem., 2008, vol. 73, pp. 5613-5616.

* cited by examiner

COMPOUND COMPRISING AROMATIC RING HAVING SULFONAMIDE AND ION TRANSPORT GROUP, POLYMER COMPRISING SAME, AND POLYELECTROLYTE MEMBRANE USING SAME

TECHNICAL FIELD

This application claims priority to and the benefit of Korean Patent Application No. 10-2015-0011994 filed in the Korean Intellectual Property Office on Jan. 26, 2015, the entire contents of which are incorporated herein by reference.

The present specification relates to a compound comprising an aromatic ring, a polymer comprising the same, and a polyelectrolyte membrane using the same.

BACKGROUND ART

A fuel cell is an energy conversion device that converts chemical energy of fuel directly into electrical energy. That is, the fuel cell uses a fuel gas and an oxidizing agent, and adopts a method of producing electric power by using electrons generated during the redox reaction of the fuel gas and the oxidizing agent. A membrane-electrode assembly (MEA) of the fuel cell is a part in which an electrochemical reaction of hydrogen and oxygen occurs, and is composed of a cathode, an anode, and an electrolyte membrane, that is, an ion conductive electrolyte membrane.

A redox flow battery (oxidation-reduction flow battery) is an electrochemical power storage device that stores chemical energy of an active material directly into electrical energy by using a system in which the active material included in an electrolytic solution is oxidized and reduced and thus the battery is charged and discharged. A unit cell of the redox flow battery comprises an electrode, an electrolyte, and an ion exchange membrane (electrolyte membrane).

Fuel cells and redox flow batteries have been researched and developed as a next-generation energy source due to high energy efficiency and eco-friendly characteristics producing less emission of contaminants.

The most essential constituent element of the fuel cells and the redox flow batteries is a polyelectrolyte membrane capable of exchanging cations, and the polyelectrolyte membrane may have characteristics of 1) excellent proton conductivity, 2) prevention of crossover of the electrolyte, 3) strong chemical resistance, 4) strengthening of mechanical properties and/or 4) a low swelling ratio. The polyelectrolyte membrane is classified into fluorine-based, partial fluorine-based, hydrocarbon-based, and the like, and the partial fluorine-based polyelectrolyte membrane has a fluorine-based main chain, and thus has advantages in that physical and chemical stabilities are excellent and thermal stability is high. Further, the partial fluorine-based polyelectrolyte membrane has advantages of both a hydrocarbon-based polyelectrolyte membrane and a fluorine-based polyelectrolyte membrane because a cation transport functional group is attached to the ends of a fluorine-based chain similarly to a fluorine-based polyelectrolyte membrane.

When operated under low humidity conditions, a fuel cell and/or a redox flow battery have/has various advantages in that reactivity of a positive electrode is improved, and a hydroplaning phenomenon and contamination of a catalyst are lowered, and the like. However, a generally used polyelectrolyte membrane has a problem in that the battery performance rapidly deteriorates because physical properties such as cation conductivity are decreased under low humidity conditions. Therefore, there is a need for studies to solve the above-mentioned problems.

PATENT DOCUMENT

Korean Patent Application Laid-Open No. 2003-0076057

DETAILED DESCRIPTION OF THE INVENTION

Technical Problem

The present specification has been made in an effort to provide a compound comprising an aromatic ring and a polyelectrolyte membrane using the same.

Technical Solution

An exemplary embodiment of the present specification provides a compound comprising an aromatic ring represented by the following Chemical Formula 1:

[Chemical Formula 1]

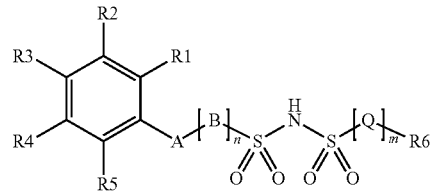

in Chemical Formula 1,

A is a direct bond, S, O, NH, or $SO_2$,

B and Q are the same as or different from each other, and are each independently represented by the following Chemical Formula 2 or 3,

[Chemical Formula 2]

[Chemical Formula 3]

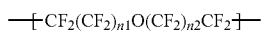

n is an integer from 1 to 16, m, n1, and n2 are each an integer from 0 to 16, when n and m are each an integer of 2 or more, a plurality of structures in the parenthesis is the same as or different from each other, two to four of R1 to R5 are the same as or different from each other, and are each independently a hydroxy group or a halogen group, and the other(s) is/are hydrogen, R6 is selected from the group consisting of —$SO_3H$, —$SO_3^-M^+$, —COOH, —$COO^-M^+$, —$PO_3H_2$, —$PO_3H^-M^+$, —$PO_3^{2-}2M^+$, and a group represented by the following Chemical Formula 4,

[Chemical Formula 4]

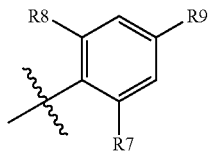

in Chemical Formula 4, at least one of R7 to R9 is selected from the group consisting of —SO$_3$H, —SO$_3^-$M$^+$, —COOH, —COO$^-$M$^+$, —PO$_3$H$_2$, —PO$_3$H$^-$M$^+$, and —PO$_3^{2-}$2M$^+$, and the others are hydrogen,

is a moiety bonded to Q of Chemical Formula 1, and

M is a Group 1 element.

An exemplary embodiment of the present specification provides a polymer comprising a monomer derived from the compound of Chemical Formula 1.

An exemplary embodiment of the present specification provides a polyelectrolyte membrane which comprises the polymer comprising a monomer derived from the compound of Chemical Formula 1.

Further, an exemplary embodiment of the present specification provides a membrane-electrode assembly comprising: an anode; a cathode; and the above-described polyelectrolyte membrane disposed between the anode and the cathode.

In addition, an exemplary embodiment of the present specification provides a polyelectrolyte-type fuel cell comprising: the above-described two or more membrane-electrode assemblies;

a stack which comprises a bipolar plate disposed between the membrane-electrode assemblies;

a fuel supplying part which supplies fuel to the stack; and an oxidizing agent supplying part which supplies an oxidizing agent to the stack.

An exemplary embodiment of the present specification also provides a redox flow battery comprising:

a positive electrode cell comprising a positive electrode and a positive electrode electrolytic solution;

a negative electrode cell comprising a negative electrode and a negative electrode electrolytic solution; and the above-described polyelectrolyte membrane disposed between the positive electrode cell and the negative electrode cell.

Advantageous Effects

A polyelectrolyte membrane manufactured by using a polymer comprising a monomer derived from a compound according to an exemplary embodiment of the present specification has excellent ion conductivity.

Further, a polyelectrolyte membrane manufactured by using a polymer comprising a monomer derived from a compound according to an exemplary embodiment of the present specification has at least two acid units per unit structure, and thus has a high ion exchange capacity (IEC) value, and as a result, the ion conductivity may be improved under high humidity and/or low humidity conditions.

In addition, a fuel cell and/or a redox flow battery, which comprise(s) the polyelectrolyte membrane, have/has excellent durability and efficiency.

BEST MODE

Figure 1:
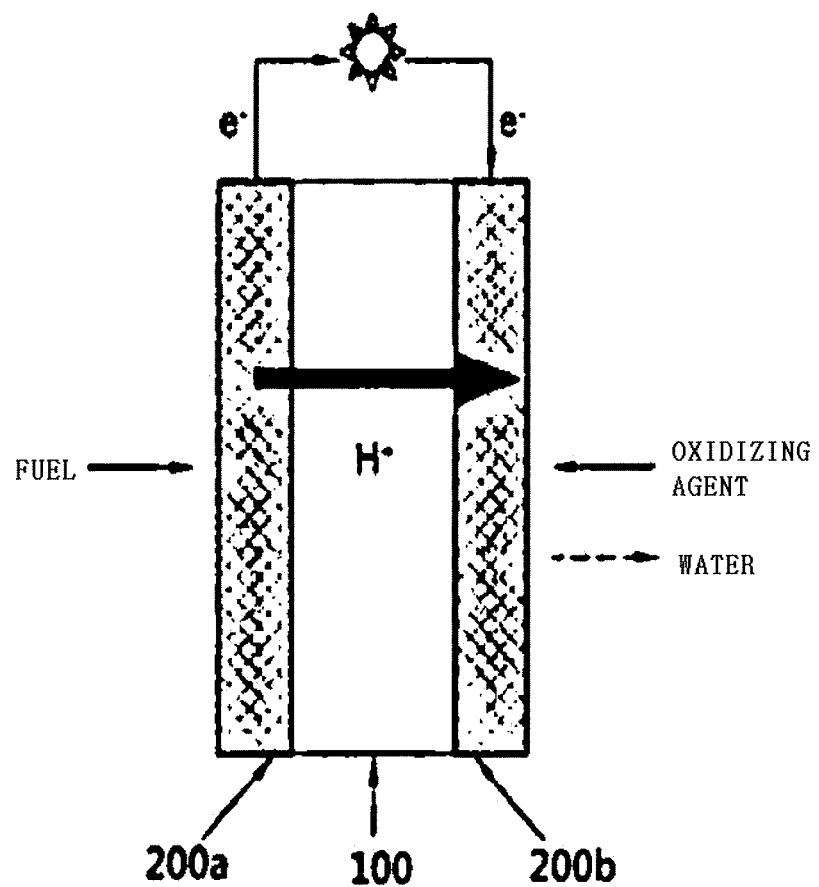
FIG. 1 is a schematic view illustrating the electricity generation principle of a fuel cell.

Hereinafter, the present specification will be described in more detail.

A generally used polyelectrolyte membrane exhibits excellent efficiency in a high humidity state, but has a problem in that cation conductivity is reduced under low humidity conditions. However, the present specification may alleviate the problems by using the above-described compound represented by Chemical Formula 1.

Specifically, in the present specification, the compound represented by Chemical Formula 1 comprises a linker which links two benzene rings comprising disulfonamide (—SO$_2$NHSO$_2$—) which may act as an acid, and an acid or a benzene ring substituted with at least one acid at the ends of the linker. The acid is an ion transport functional group, and is selected from the group consisting of —SO$_3$H, —SO$_3^-$M$^+$, —COOH, —COO$^-$M$^+$, —PO$_3$H$_2$, —PO$_3$H$^-$M$^+$, and —PO$_3^{2-}$2M$^+$. Accordingly, a polymer comprising a monomer derived from the compound represented by Chemical Formula 1 exhibits the increased number of acids per unit, and the ion exchange capacity (IEC) value of a polyelectrolyte membrane comprising the polymer may be increased. Consequently, the polyelectrolyte membrane may exhibit excellent cation conductivity under not only high humidity conditions, but also low humidity conditions.

According to an exemplary embodiment of the present specification, M being a Group 1 element may be Li, Na, or K.

According to an exemplary embodiment of the present specification, two of R1 to R5 are a halogen group. In this case, the halogen group may be chlorine or fluorine.

According to an exemplary embodiment of the present specification, in Chemical Formula 1, R1 and R5 are a halogen group, and R2 to R4 are hydrogen.

According to an exemplary embodiment of the present specification, in Chemical Formula 1, R2 and R5 are a halogen group, and R1, R3, and R4 are hydrogen.

According to an exemplary embodiment of the present specification, in Chemical Formula 1, R3 and R5 are a halogen group, and R1, R2, and R4 are hydrogen.

According to another exemplary embodiment, in Chemical Formula 1, R2 and R4 are a halogen group or a hydroxy group, and R1, R3, and R5 are hydrogen.

According to an exemplary embodiment of the present specification, three of R1 to R5 are a halogen group, and the others are hydrogen. In this case, the halogen group may be chlorine or fluorine.

According to an exemplary embodiment of the present specification, four of R1 to R5 are a halogen group, and the other is hydrogen. In this case, the halogen group may be chlorine or fluorine.

According to an exemplary embodiment of the present specification, in Chemical Formula 1, R6 is disposed at the ortho and/or the para position(s) in a relationship between Chemical Formula 4 and a carbon in which a linker, which links two benzene rings, is substituted in R7 to R9 of Chemical Formula 4. The linker, which links two benzene rings, comprises a functional group exhibiting an electron withdrawing effect and/or a heteroatom, and the acidity of an ion transport functional group (R6 to R8) disposed at the ortho and/or the para position(s) with respect to the functional group and the heteroatom is increased. Consequently, a polyelectrolyte membrane comprising a polymer comprising the compound has an advantage in that improved cation conductivity may be exhibited.

According to an exemplary embodiment of the present specification, in Chemical Formula 1, A is S, O, or $SO_2$. In this case, there is an advantage in that a compound comprising an aromatic ring represented by Chemical Formula 1, is more readily synthesized. According to an exemplary embodiment of the present specification, in Chemical Formula 1, A is a direct bond.

According to an exemplary embodiment of the present specification, in Chemical Formula 1, A is S.

According to an exemplary embodiment of the present specification, in Chemical Formula 1, A is O.

According to an exemplary embodiment of the present specification, A is O or $SO_2$. Due to the chemical stability of a sulfonyl group or an ether group, which is not easily decomposed by a strong acid of an electrolyte or radicals produced from an electrolyte, when A is O or $SO_2$, an electrolyte membrane comprising the compound may exhibit improved durability. In particular, in the case of a redox flow battery, vanadium of the electrolyte serves as an oxidizing agent, and as result, A is most preferably O or $SO_2$ in order to prevent a problem in that S is oxidized into SO (sulfoxide) and thus may be easily decomposed when A being a linker is S.

According to an exemplary embodiment of the present specification, A is NH.

According to an exemplary embodiment of the present specification, B may be represented by Chemical Formula 2. In this case, it is preferred that Chemical Formula 2 is represented by the following Chemical Formula 2-1.

[Chemical Formula 2-1]

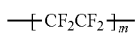

In Chemical Formula 2-1, m is an integer from 1 to 8.

According to another exemplary embodiment, B may be represented by Chemical Formula 3.

In the present specification, when n is 2 or more, a plurality of B's is the same as or different from each other. For example, when n is 2, both the B's may also be represented by Chemical Formula 2, both the B's may also be represented by Chemical Formula 3, one B may be represented by Chemical Formula 2, and the other B may be represented by Chemical Formula 3.

According to an exemplary embodiment of the present specification, in Chemical Formula 4, at least one of R7 to R9 is an ion transport functional group, and the ion transport functional group is disposed at the ortho and/or the para position(s) in a relationship with a linker (-A-[B]$_n$—$SO_2NHSO_2$-[Q]$_m$-) which links two benzene rings. As described above, the ion transport functional group is disposed at the ortho and/or the para position(s), thereby exhibiting improved reactivity during the polymerization reaction.

According to an exemplary embodiment of the present specification, at least one of R7 to R9 is —$SO_3H$ or —$SO_3$-$M^+$. A sulfonic acid group absorbs a maximum of about 10 mole of water per mole, and thus exhibits a high proton conductivity of about 0.1 $Scm^{-1}$.

According to an exemplary embodiment of the present specification, in Chemical Formula 1, n is 1.

According to an exemplary embodiment of the present specification, in Chemical Formula 1, n may be 2 or more. When B is represented only by Chemical Formula 2, n is preferably an integer of 2 or more.

According to an exemplary embodiment of the present specification, m is an integer from 0 to 2, and when m is 2, a plurality of Q's is the same as or different from each other.

According to another exemplary embodiment of the present specification, in Chemical Formula 3, n1 and n2 are 1.

According to an exemplary embodiment of the present specification, the compound represented by Chemical Formula 1 may be any one selected from the following structures.

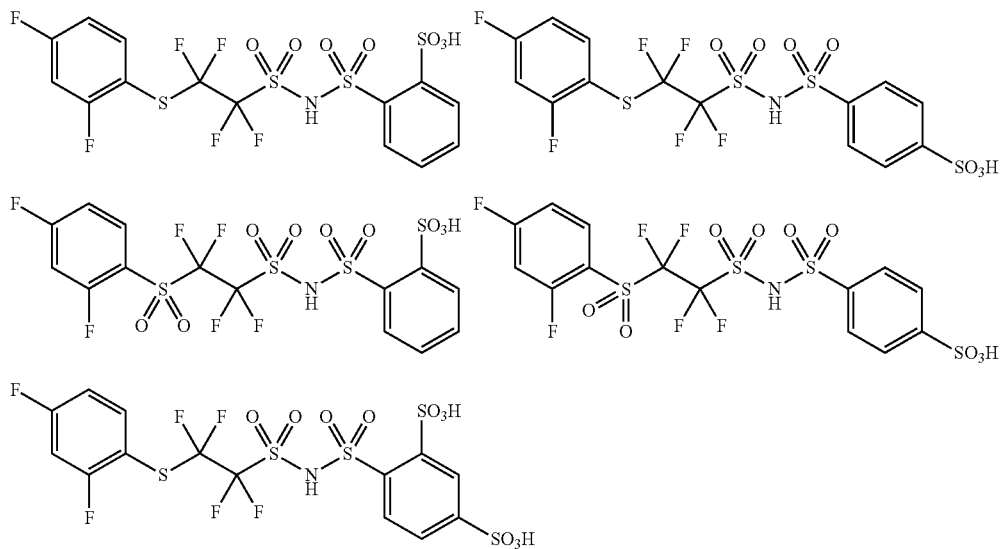

-continued
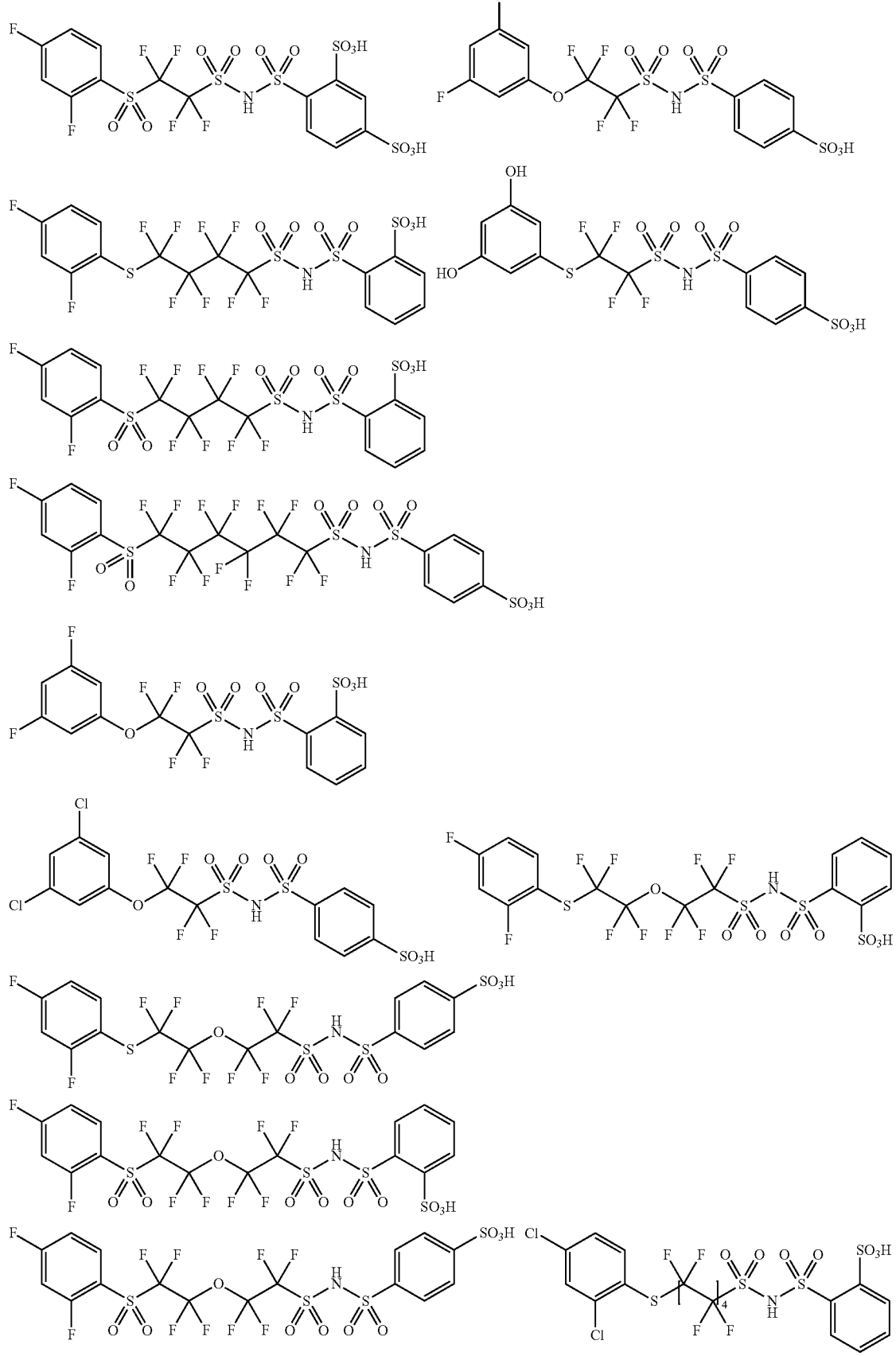

-continued
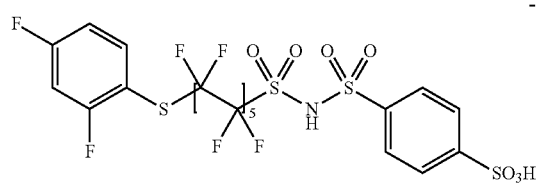
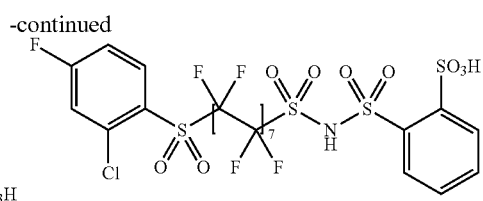
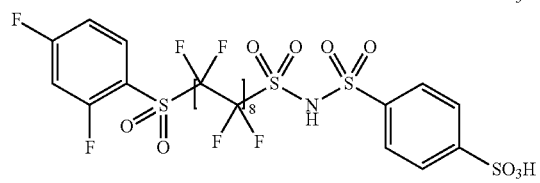
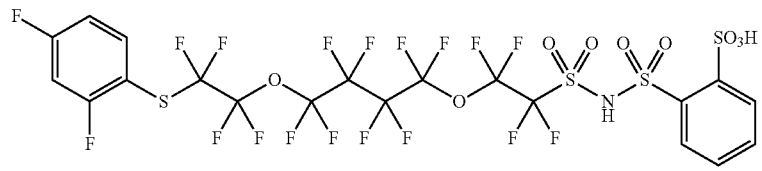
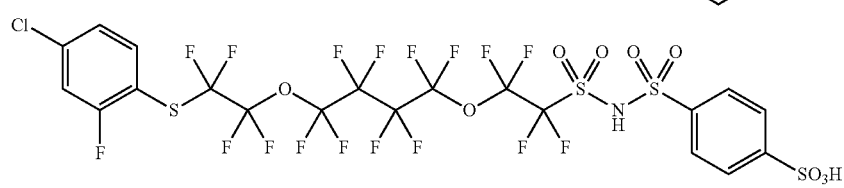
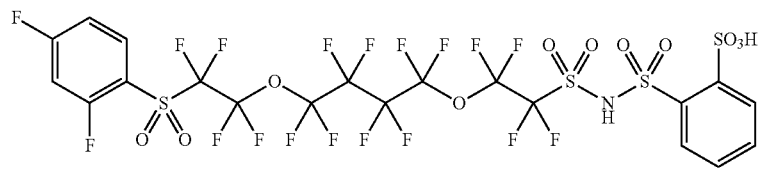
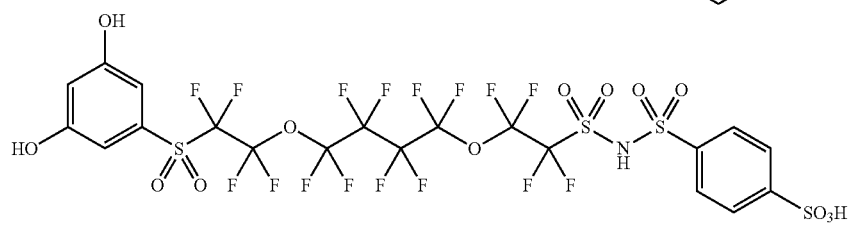
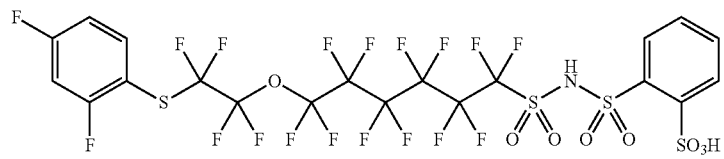
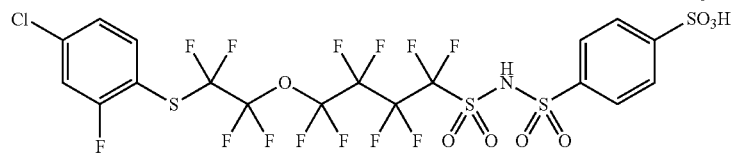
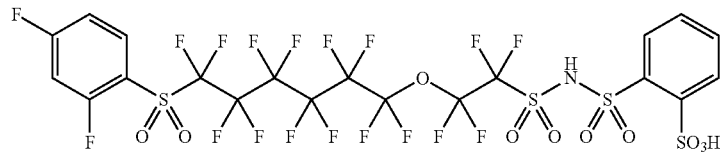
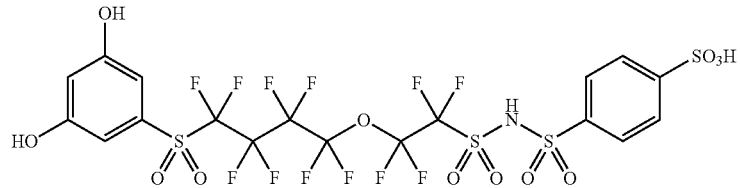

-continued
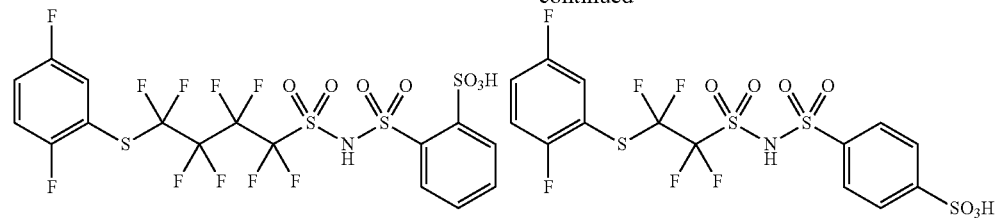
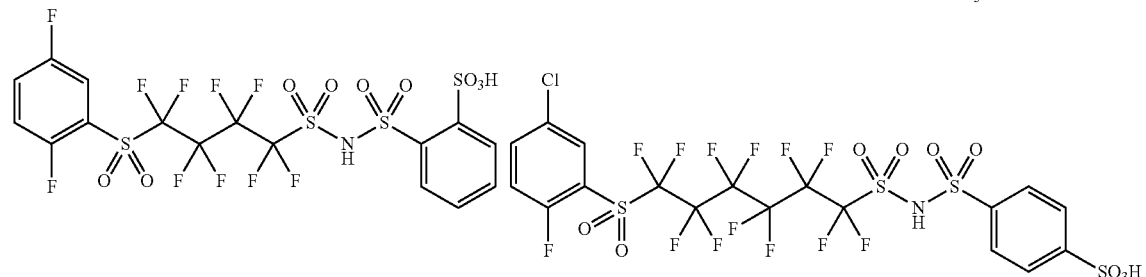
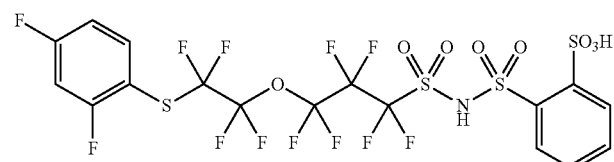
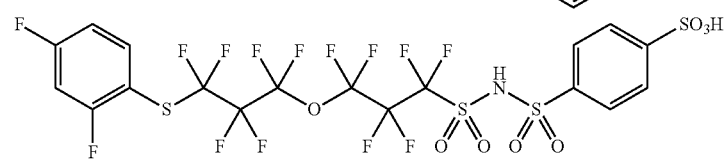
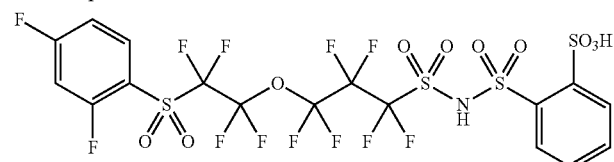
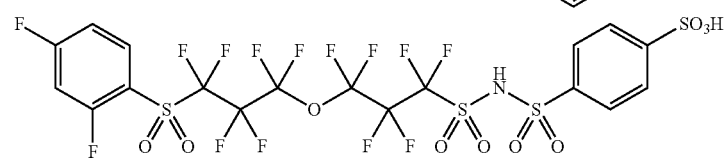
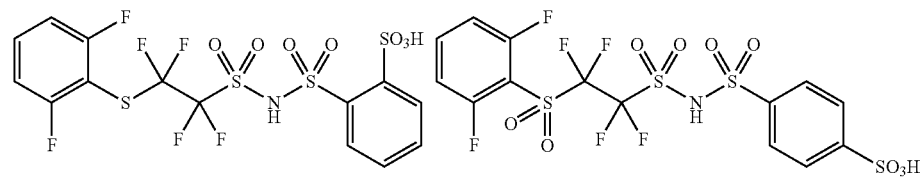
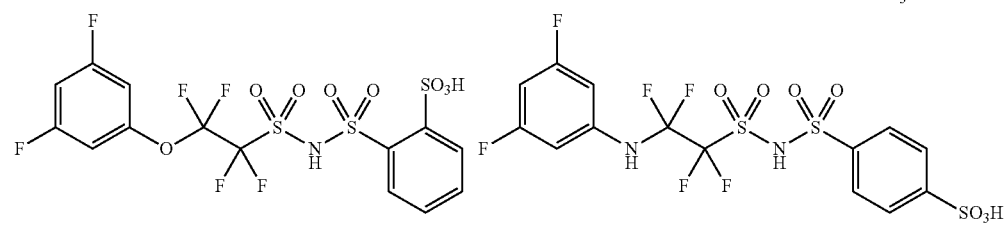
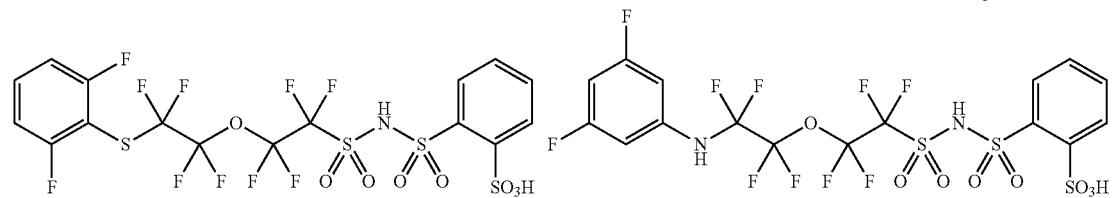

-continued

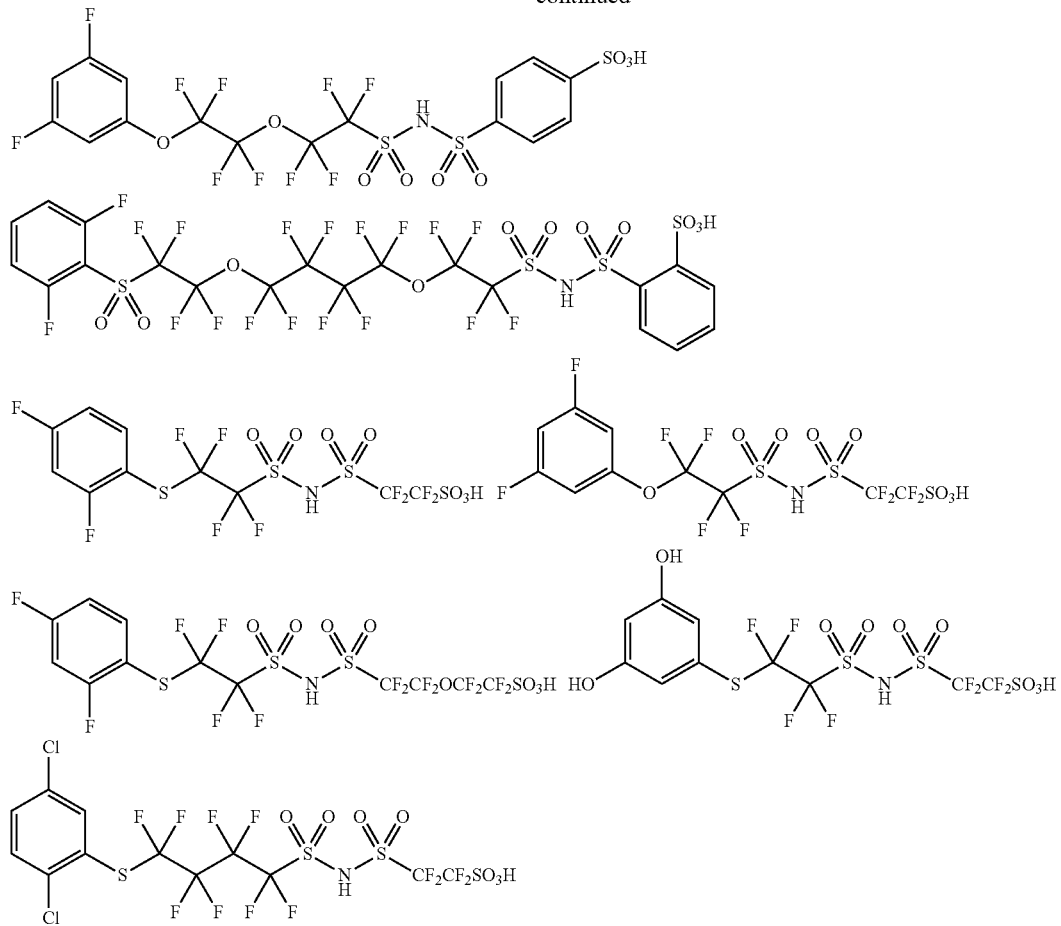

The compound represented by Chemical Formula 1 may be prepared based on Preparation Examples to be described below.

An exemplary embodiment of the present specification provides a polymer comprising a monomer derived from the compound represented by Chemical Formula i. The aforementioned monomer has an advantage in that improved reactivity is exhibited during the polymerization reaction as described above.

In the present specification, the "monomer" means a structure in which a compound is included in the form of a divalent or more group in a polymer by a polymerization reaction. Specifically, a monomer derived from the compound represented by Chemical Formula 1 may have the following structures. However, the structures are not limited thereto.

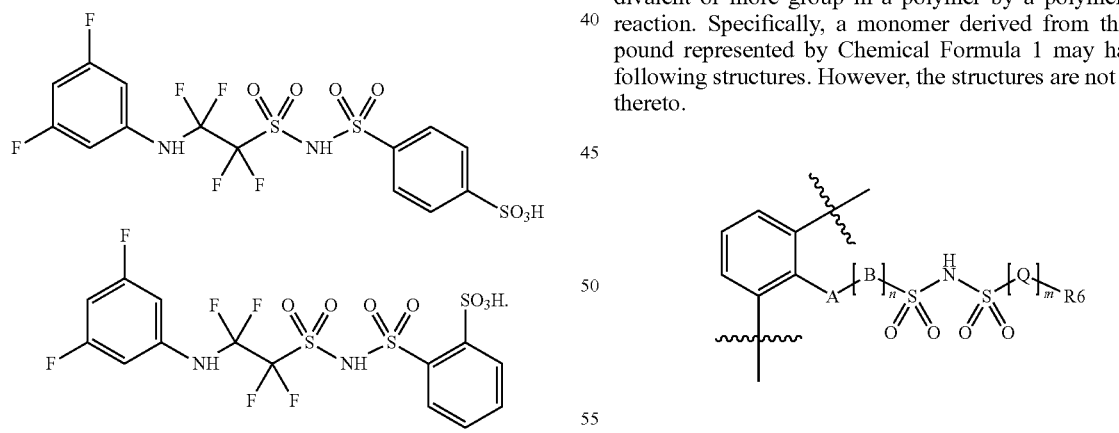

-continued

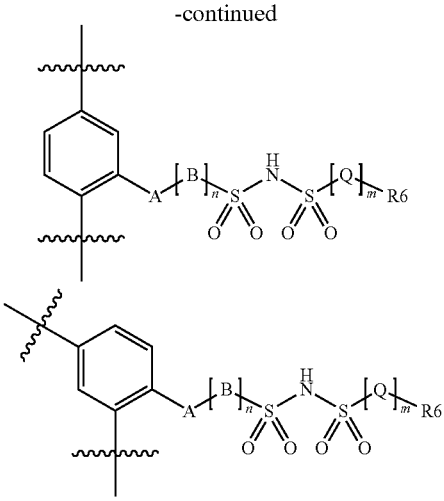

The polymer according to an exemplary embodiment of the present specification comprises a monomer derived from the compound represented by Chemical Formula 1 as described above. Accordingly, since an ion transport functional group comprising a partial fluorine-based monomer is present in the form of a pendant in the polymer, ion transport functional groups are gathered well in the polymer, and facilitate phase separation to easily form ion channels, and as a result, it is possible to implement an effect in that the ion conductivity of a polyelectrolyte membrane comprising the polymer is improved. Further, since the polymer comprises at least two acid units per unit structure of a monomer, an effect of improving ion conductivity is much better.

According to an exemplary embodiment of the present specification, the polymer may be a random polymer. In this case, a polymer having a high molecular weight may be obtained by a simple polymerization method.

In this case, a monomer derived from the compound represented by Chemical Formula 1 serves to adjust the ion conductivity of a polyelectrolyte membrane comprising the polymer, and a co-monomer in the other ratio to be randomly polymerized serves to improve the mechanical strength.

According to an exemplary embodiment of the present specification, a monomer derived from the compound represented by Chemical Formula 1 may be included in an amount of 0.1 mol % to 100 mol % based on the entire polymer. Specifically, a polymer only comprises a monomer derived from the compound represented by Chemical Formula 1. In another exemplary embodiment, the polymer may further comprise a second monomer in addition to a monomer derived from the compound represented by Chemical Formula 1. In this case, the content of a monomer derived from the compound represented by Chemical Formula 1 is preferably 0.5 mol % to 65 mol %. More preferably, the content thereof may be 5 mol % to 65 mol %. A polymer comprising a monomer derived from a compound within the range has a mechanical strength and high ion conductivity.

As the second monomer, those known in the art may be used. In this case, one or two or more second monomers may be used.

As an example of the second monomer, it is possible to use a monomer constituting a perfluorosulfonic acid polymer, a hydrocarbon-based polymer, polyimide, polyvinylidene fluoride, polyethersulfone, polyphenylene sulfide, polyphenylene oxide, polyphosphazene, polyethylene naphthalate, polyester, doped polybenzimidazole, polyether ketone, polysulfone, acids thereof or bases thereof.

According to an exemplary embodiment of the present specification, the content of the second monomer in the polymer may be more than 0 wt % and 99.9 wt % or less.

According to an exemplary embodiment of the present specification, when the polymer comprises the second monomer, the polymer may be a random polymer.

According to an exemplary embodiment of the present specification, the polymer is represented by the following Chemical Formula 5.

[Chemical Formula 5]

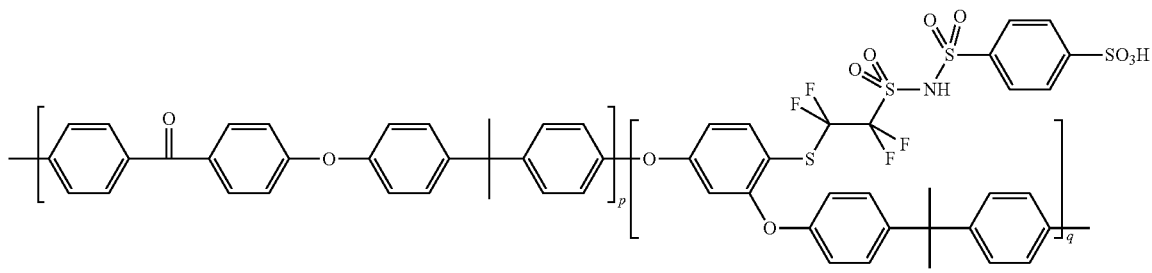

In Chemical Formula 5,
p and q are each more than 0 and less than 1, and p+q=1.

An exemplary embodiment of the present specification also provides a polyelectrolyte membrane comprising the polymer. The polyelectrolyte membrane may exhibit the above-described effects.

In the present specification, the "electrolyte membrane" is a membrane which may exchange ions, and comprises a membrane, an ion exchange membrane, an ion transport membrane, an ion conductive membrane, a separation membrane, an ion exchange separation membrane, an ion transport separation membrane, an ion conductive separation membrane, an ion exchange electrolyte membrane, an ion transport electrolyte membrane, or an ion conductive electrolyte membrane, and the like.

The polyelectrolyte membrane according to the present specification may be manufactured by using materials and/or methods known in the art, except that the polyelectrolyte membrane comprises the monomer derived from the compound represented by Chemical Formula 1.

According to another exemplary embodiment, the polymer included in the polyelectrolyte membrane may have a weight average molecular weight of 500 or more and 5,000,000 or less (g/mol), specifically 20,000 or more and 2,000,000 or less (g/mol).

When the copolymer has a weight average molecular weight of 500 or more and 5,000,000 or less (g/mol), mechanical properties of an electrolyte membrane do not deteriorate, and an appropriate solubility of the polymer may be maintained to easily manufacture the electrolyte membrane.

According to an exemplary embodiment of the present specification, the polyelectrolyte membrane has an ion exchange capacity (IEC) value of 0.01 mmol/g to 7 mmol/g.

When the polyelectrolyte membrane has the ion exchange capacity (IEC) value within the range, ion channels are formed in the polyelectrolyte membrane, and the polymer may exhibit ion conductivity.

According to an exemplary embodiment of the present specification, the electrolyte membrane may have a thickness of 1 µm to 500 µm, specifically, 5 µm to 200 µm. When the electrolyte membrane has a thickness of 1 µm to 500 µm, an electric short and a crossover of an electrolyte material may be reduced, and excellent positive ion conductivity characteristics may be exhibited.

According to an exemplary embodiment of the present specification, the polyelectrolyte membrane may have ion conductivity of 0.001 S/cm or more and 0.5 S/cm or less, specifically 0.01 S/cm or more and 0.5 S/cm or less.

According to another exemplary embodiment, the ion conductivity of the polyelectrolyte membrane may be measured under humid conditions. The humid condition may also mean a full humidity condition, may also mean a relative humidity (RH) of 10% to 100%, and may also mean a relative humidity (RH) of 30% to 100%.

According to an exemplary embodiment of the present specification, the polyelectrolyte membrane may have ion conductivity of 0.001 S/cm or more and 0.5 S/cm or less, and may be measured at a relative humidity (RH) of 10% to 100%. According to another exemplary embodiment, the polyelectrolyte membrane may have ion conductivity of 0.01 S/cm or more and 0.5 S/cm or less, and may be measured at a relative humidity (RH) of 30% to 100%.

According to an exemplary embodiment of the present specification, at least a part of the polymer may be in the form of a metal salt. Further, the metal salt may be substituted in the form of an acid.

Specifically, it is possible to form an electrolyte membrane comprising a polymer substituted with H (hydrogen) instead of a metal M, by adding an acid solution to a polymer in which at least one of R7 to R9 in Chemical Formula 1 is —$SO_3^-M^+$, —$COO-M^+$, —$PO_3HM^+$, or —$PO_3^{2-}2M^+$.

According to an exemplary embodiment of the present specification, the acid solution may be a general acid solution used in the acid treatment, and may be specifically hydrochloric acid or sulfuric acid.

According to an exemplary embodiment of the present specification, the concentration of the acid solution may be 0.1 M or more and 10 M or less, specifically, 1 M or more and 2 M or less. When the concentration of the acid solution is 0.1 M or more and 10 M or less, the polymer may be easily substituted with hydrogen instead of M without damaging the electrolyte membrane.

An exemplary embodiment of the present specification also provides a membrane-electrode assembly comprising: an anode; a cathode; and the above-described polyelectrolyte membrane disposed between the anode and the cathode.

The membrane-electrode assembly (MEA) means an assembly of electrodes (a cathode and an anode) in which an electrochemical catalyst reaction of fuel and air occurs and a polymer membrane in which hydrogen ions are transported, and is a single integral-type unit in which electrodes (a cathode and an anode) and an electrolyte membrane are adhered.

The membrane-electrode assembly of the present specification is in the form in which a catalyst layer of an anode and a catalyst layer of a cathode are brought into contact with an electrolyte membrane, and may be manufactured by a typical method known in the art. As an example, the membrane-electrode assembly may be manufactured by thermally compressing, at 100° C. to 400° C., the cathode; the anode; and the electrolyte membrane positioned between the cathode and the anode in a state in which the cathode, the anode, and the electrolyte membrane are brought into close contact with each other.

An anode electrode may comprise an anode catalyst layer and an anode gas diffusion layer. The anode gas diffusion layer may comprise an anode micro porous layer and an anode electrode substrate.

A cathode electrode may comprise a cathode catalyst layer and a cathode gas diffusion layer. The cathode gas diffusion layer may comprise a cathode micro porous layer and a cathode electrode substrate.

FIG. 1 schematically illustrates the electricity generation principle of a fuel cell, and in the fuel cell, the most fundamental unit of generating electricity is a membrane-electrode assembly (MEA), and the membrane-electrode assembly is composed of an electrolyte membrane 100 and electrodes of an anode 200a and a cathode 200b formed on both surfaces of the electrolyte membrane 100.

Referring to FIG. 1 which illustrates the elasticity generation principle of a fuel cell, an oxidation reaction of fuel such as hydrogen or a hydrocarbon such as methanol and butane occurs in the anode 200a, and as a result, hydrogen ions ($H^+$) and electrons ($e^-$) are generated, and the hydrogen ions move to the cathode 200b through the electrolyte membrane 100. In the cathode 200b, hydrogen ions transported through the electrolyte membrane 100, an oxidizing agent such as oxygen, and electrons are reacted to produce water. Electrons move to an external circuit by the reaction.

The catalyst layer of the anode electrode is a site where an oxidation reaction of fuel occurs, and it is possible to preferably use a catalyst selected from the group consisting of platinum, ruthenium, osmium, a platinum-ruthenium alloy, a platinum-osmium alloy, a platinum-palladium alloy, and a platinum-transition metal alloy. The catalyst layer of the cathode electrode is a site where a reduction reaction of an oxidizing agent occurs, and platinum or a platinum-transition metal alloy may be preferably used as a catalyst. The catalysts may be not only used as they are, but also used while being supported on a carbon-based carrier.

The process of introducing a catalyst layer may be carried out by a typical method known in the art, and for example, a catalyst layer may be formed by directly coating an electrolyte membrane with a catalyst ink or coating a gas diffusion layer with a catalyst ink. In this case, the coating method with a catalyst ink is not particularly limited, but it is possible to use a method such as spray coating, tape casting, screen printing, blade coating, die coating or spin coating, and the like. The catalyst ink may be representatively composed of a catalyst, a polymer ionomer, and a solvent.

The gas diffusion layer serves as both a current conductor and a channel through which reaction gases and water move, and has a porous structure. Accordingly, the gas diffusion layer may comprise a conductive substrate. As the conductive substrate, carbon paper, carbon cloth, or carbon felt may be preferably used. The gas diffusion layer may further comprise a micro porous layer between the catalyst layer and the conductive substrate. The micro porous layer may be used in order to improve the performance of a fuel cell under low humidity conditions, and serves to allow an electrolyte membrane to be maintained in a sufficiently wet state by reducing the amount of water leaving out of the gas diffusion layer.

An exemplary embodiment of the present specification provides a polyelectrolyte-type fuel cell comprising: the above-described two or more membrane-electrode assemblies; a stack which comprises a bipolar plate disposed between the membrane-electrode assemblies; a fuel supplying part which supplies fuel to the stack; and an oxidizing agent supplying part which supplies an oxidizing agent to the stack.

When the electrolyte membrane according to an exemplary embodiment of the present specification is used as an ion exchange membrane of a fuel cell, the above-described effect may be exhibited.

A fuel cell is an energy conversion device that converts chemical energy of fuel directly into electrical energy. That is, the fuel cell uses a fuel gas and an oxidizing agent, and adopts a method of producing electric power by using electrons generated during the redox reaction of the fuel gas and the oxidizing agent.

The fuel cell may be manufactured by a typical method known in the art by using the above-described membrane-electrode assembly (MEA). For example, the fuel cell may be manufactured by being composed of the membrane-electrode assembly (MEA) manufactured above and the bipolar plate.

The fuel cell of the present specification comprises a stack, a fuel supplying part, and an oxidizing agent supplying part.

Figure 3:
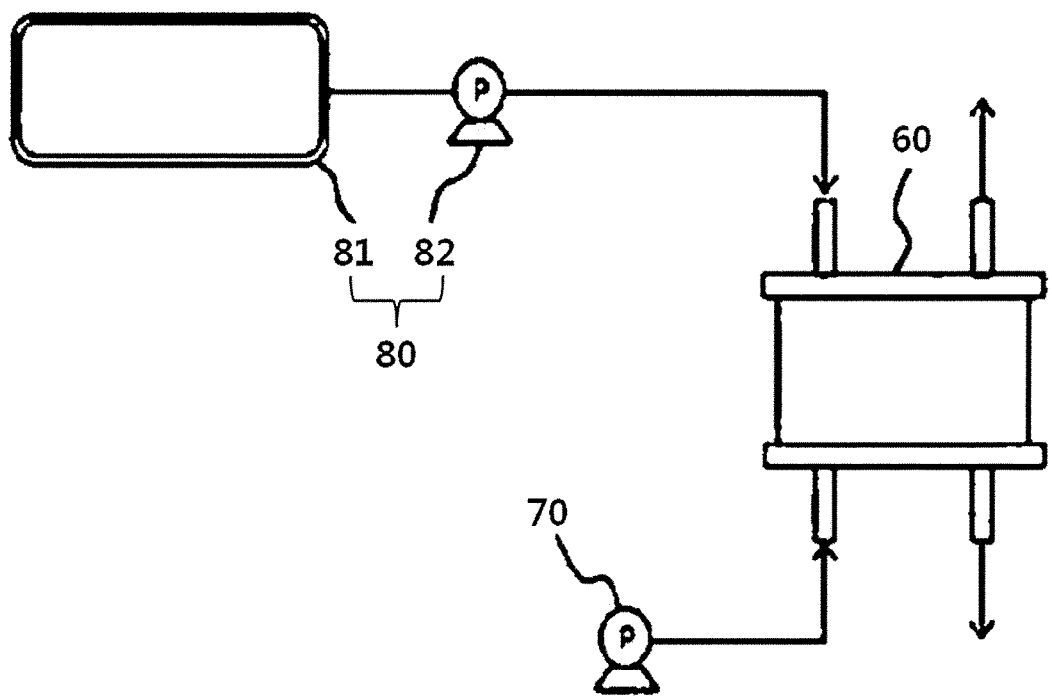
FIG. 3 is a view schematically illustrating an example of a fuel cell.

FIG. 3 schematically illustrates the structure of a fuel cell, and the fuel cell comprises a stack 60, an oxidizing agent supplying part 70, and a fuel supplying part 80.

The stack 60 comprises the aforementioned one or two or more membrane-electrode assemblies, and when two or more membrane-electrode assemblies are included, the stack 60 comprises a separator interposed therebetween. The separator serves to prevent the membrane-electrode assemblies from being electrically connected to each other, and to transport fuel and an oxidizing agent, which are supplied from the outside, to the membrane-electrode assemblies.

The oxidizing agent supplying part 70 serves to supply an oxidizing agent to the stack 60. As the oxidizing agent, oxygen is representatively used, and oxygen or air may be used by being injected into the oxidizing agent supplying part 70.

The fuel supplying part 80 serves to supply fuel to the stack 60, and may be composed of a fuel tank 81 which stores fuel, and a pump 82 which supplies the stack 60 with fuel stored in the fuel tank 81. As the fuel, hydrogen or hydrocarbon fuel in a gas or liquid state may be used. Examples of the hydrocarbon fuel include methanol, ethanol, propanol, butanol, or natural gases.

The fuel cell can be a polymer electrolyte fuel cell, a direct liquid fuel cell, a direct methanol fuel cell, a direct formic acid fuel cell, a direct ethanol fuel cell, or a direct dimethyl ether fuel cell, and the like.

Further, an exemplary embodiment of the present specification provides a redox flow battery comprising: a positive electrode cell comprising a positive electrode and a positive electrode electrolytic solution; a negative electrode cell comprising a negative electrode and a negative electrode electrolytic solution; and the polyelectrolyte membrane according to an exemplary embodiment of the present specification, which is disposed between the positive electrode cell and the negative electrode cell.

A redox flow battery (oxidation-reduction flow battery) is an electrochemical power storage device that stores chemical energy of an active material directly into electrical energy by using a system in which the active material included in an electrolytic solution is oxidized and reduced and thus the battery is charged and discharged. The redox flow battery uses a principle in which when electrolytic solutions comprising active materials having different oxidation states meet each other with an ion exchange membrane interposed therebetween, electrons are given and received, and thus the battery is charged and discharged. In general, the redox flow battery is composed of a tank which contains an electrolytic solution, a battery cell in which the charge and discharge occur, and a circulation pump which circulates the electrolytic solution between the tank and the battery cell, and the unit cell of the battery cell comprises an electrode, an electrolyte, and an ion exchange membrane.

When the electrolyte membrane according to an exemplary embodiment of the present specification is used as an ion exchange membrane of a redox flow battery, the above-described effect may be exhibited.

The redox flow battery of the present specification may be manufactured by a typical method known in the art, except that the redox flow battery comprises the polyelectrolyte membrane according to an exemplary embodiment of the present specification.

Figure 2:
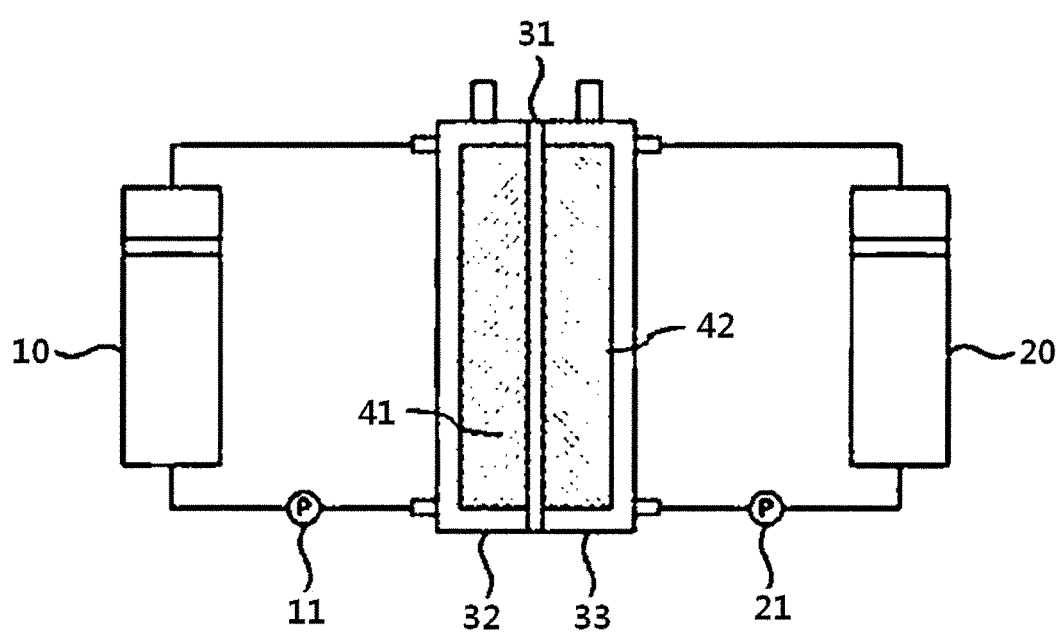
FIG. 2 is a view schematically illustrating a general structure of a redox flow battery.

As illustrated in FIG. 2, the redox flow battery is divided into a positive electrode cell 32 and a negative electrode cell 33 by an electrolyte membrane 31. The positive electrode cell 32 and the negative electrode cell 33 comprise a positive electrode and a negative electrode, respectively. The positive electrode cell 32 is connected to a positive electrode tank 10 for supplying and releasing a positive electrode electrolytic solution 41 through pipes.

The negative electrode cell 33 is also connected to a negative electrode tank 20 for supplying and releasing a negative electrode electrolytic solution 42 through pipes. The electrolytic solution is circulated through pumps 11 and 21, and an oxidation/reduction reaction (that is, a redox reaction) in which the oxidation number of ions is changed occurs, and as a result, the charge and discharge occur in the positive electrode and the negative electrode.

An exemplary embodiment of the present specification also provides a method for manufacturing the electrolyte membrane. For the method for manufacturing the electrolyte membrane, the polyelectrolyte membrane may be manufactured by using materials and/or methods in the art, except that the polyelectrolyte membrane comprises the polymer comprising the monomer derived from the compound represented by Chemical Formula 1. For example, a polyelectrolyte membrane may be manufactured by adding polymer to a solvent to make a polymer solution, and then forming a film using a solvent casting method.

EXPLANATION OF REFERENCE NUMERALS AND SYMBOLS

100: Electrolyte membrane
200a: Anode
200b: Cathode
10: Positive electrode tank and 20: Negative electrode tank
11, 21: Pump
31: Electrolyte membrane 32: Positive electrode cell
33: Negative electrode cell
41: Positive electrode electrolytic solution
42: Negative electrode electrolytic solution
60: Stack
70: Oxidizing agent supplying part
80: Fuel supplying part
81: Fuel tank
82: Pump

MODE FOR INVENTION

Hereinafter, the present specification will be described in more detail through Examples. However, the following Examples are provided for exemplifying the present specification, and the scope of the present specification is not limited thereby.

<Preparation Example 1> Preparation of 2-((2,4-difluorophenyl)thio)-1,1,2,2-tetrafluoroethane-1-sulfonamide

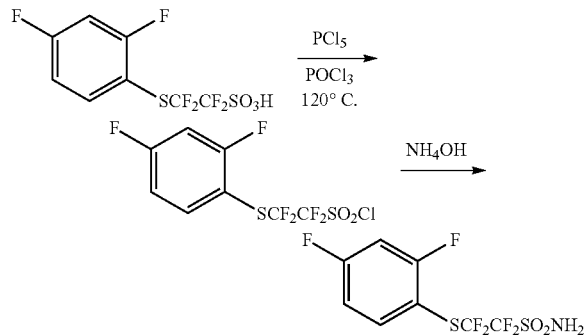

10 g (30.65 mmol) of 2-((2,4-difluorophenyl)thio)-1,1,2,2-tetrafluoroethane-1-sulfonic acid was dissolved in 100 ml of $POCl_3$, and then 15.32 g (73.57 mmol) of $PCl_5$ was added thereto, and the resulting mixture was heated to 120° C. The reactant was stirred at 120° C. for 1 hour, and then warmed, further stirred at 150° C. for 2 hours, and cooled to room temperature. The reactant was vacuum distilled under high pressure to remove an excessive amount of $POCl_3$, and then dissolved in $CH_2Cl_2$ and washed several times with water at 0° C. The organic layer was dried over $MgSO_4$, and vacuum distilled to obtain a crude sulfonyl chloride compound. The sulfonyl chloride compound was dissolved in $CH_2Cl_2$ without a separate purification process and cooled to 0° C., and then 100 ml of ammonia water was slowly added dropwise thereto. The mixture was reacted at room temperature for 16 hours by slowly increasing the temperature, and vacuum distilled under high pressure. In this case, the obtained compound was dissolved in ethyl acetate, and then the resulting mixture was washed several times with water, the organic layer was dried over $MgSO_4$ and vacuum distilled to obtain 4.58 g (45.9%) of the aforementioned compound.

1H NMR (500 MHz, DMSO-D6) δ 8.78 (2H, brs), 7.83 (1H, m), 7.56 (1H, m), 7.28 (1H, m)
Mass 326 (M+H)

<Preparation Example 2> Preparation of 4-(N-((2-((2,4-difluorophenyl)thio)-1,1,2,2-tetrafluoro ethyl)sulfonyl)sulfamoyl)benzenesulfonyl chloride

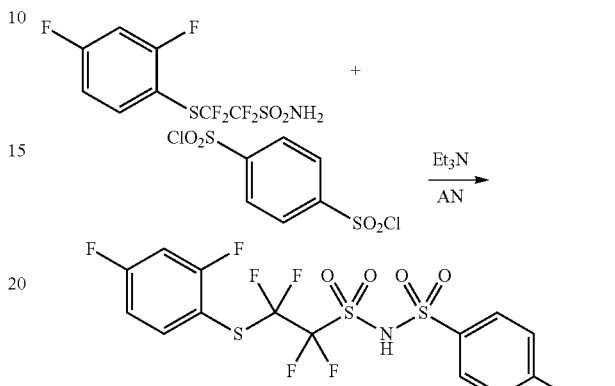

4.58 g (14.1 mmol) of the sulfonamide obtained in Preparation Example 1 was dissolved in 40 ml of acetonitrile, and then 4.26 g (15.5 mmol) of 1,4-benzenedisulfonyl chloride was added thereto, and the reactant was cooled to 0° C. 5.89 ml (42.2 mol) of $Et_3N$ was slowly added dropwise to the reactant at 0° C., and then the resulting mixture was stirred for 1 to 2 hours by being slowly warmed to room temperature. A crude compound obtained by vacuum distilling the mixture to remove the solvent was dissolved in ethyl acetate, and then the resulting solution was washed several times with 1 N HCl and $Et_3N$ was removed. The organic layer was separated, dried over $MgSO_4$ and distilled, and then the residue was separated and purified with column chromatography using methylene chloride:methyl alcohol=9:1 to obtain 6.75 g (85%) of the aforementioned compound.

1H NMR (500 MHz, DMSO-D6) δ 9.20 (1H, brs), 8.05 (4H, m), 7.74 (1H, m), 7.49 (1H, m), 7.23 (1H, m)
Mass 564 (M+H)

<Preparation Example 3> Preparation of 4-(N-((2-((2,4-difluorophenyl)thio)-1,1,2,2-tetrafluoro ethyl)sulfonyl)sulfamoyl)benzenesulfonic acid

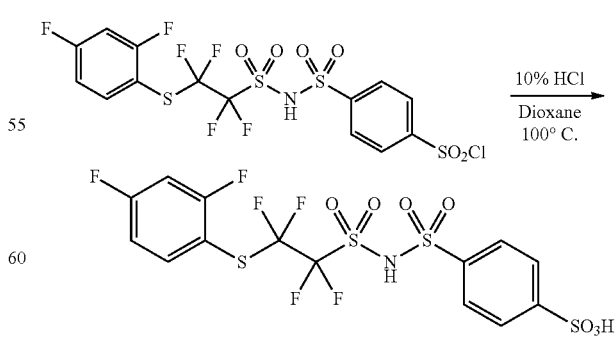

6.75 g (12.0 mmol) of 4-(N-((2-((2,4-difluorophenyl)thio)-1,1,2,2-tetrafluoro ethyl)sulfonyl)sulfamoyl)benzenesulfonyl chloride obtained in Preparation Example 2 was dissolved in 40 ml of 1,4-dioxane, and then 40 ml of 10% HCl was added thereto, and the resulting mixture was heated to 100° C. The reactant was stirred at 100° C. for 16 hours, and then cooled to room temperature, and the solvent was completely removed by means of vacuum distillation. In this case, the obtained crude compound was dissolved in $H_2O$, and then washed several times with $CH_2Cl_2$ in order to remove impurities, and the remaining aqueous layer was vacuum distilled again. The compound was dissolved in $CH_2Cl_2$, and then a solid compound obtained by slowly adding dropwise the resulting solution to n-hexane was filtered and dried under $N_2$ gas to obtain 5.62 g (86.0%) of the aforementioned compound.

1H NMR (500 MHz, DMSO-D6) δ 9.20 (1H, brs), 8.50 (1H, brs). 8.15 (2H, m), 8.05 (2H, m), 7.72 (1H, m), 7.47 (1H, m), 7.21 (1H, m)

Mass 546 (M+H)

<Example 1> Synthesis of Random Polymer

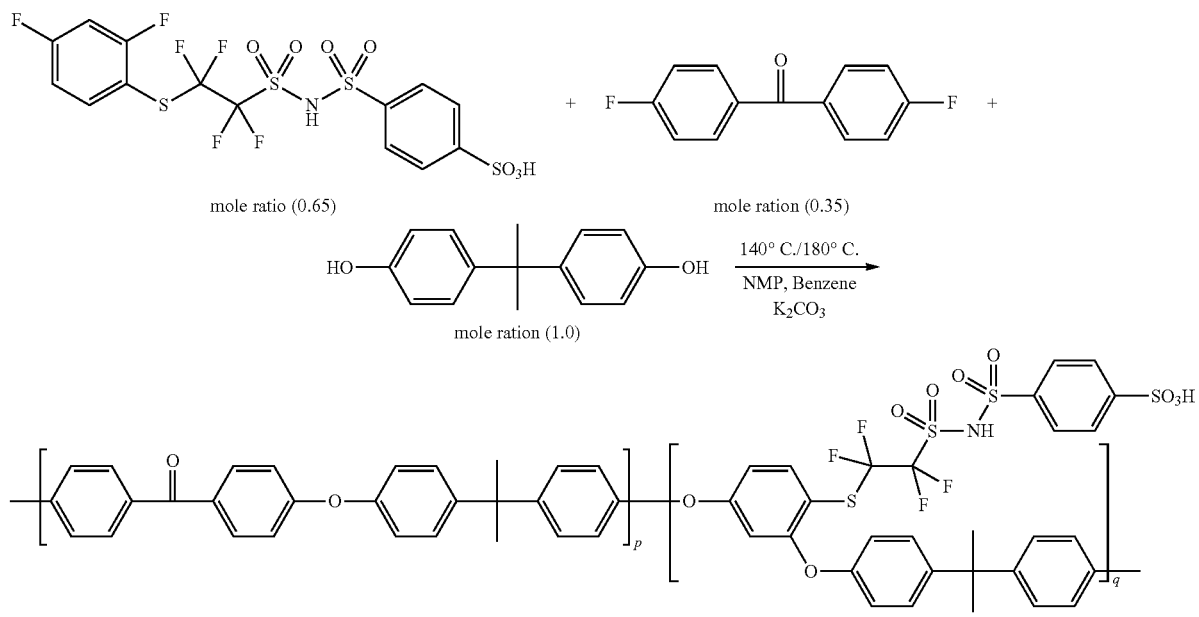

Each monomer and potassium carbonate ($K_2CO_3$: molar ratio 4) were mixed at a ratio of 20 wt % of NMP and a ratio of 20 wt % of benzene, and polymerized at 140° C. for 4 hours and at 180° C. for 16 hours to prepare the polymer.

p and q are each more than 0 and less than 1, and p+q=1.

An electrolyte membrane was manufactured by using the obtained polymer, the molecular weight was measured through GPC, and the results of measuring the cation conductivity and ion exchange capacity (IEC) of the pure film are described.

TABLE 1

| | Mn (g/mol) | Mw (g/mol) | Mw/Mn | Ion conductivity (S/m) | IEC |
|---|---|---|---|---|---|
| Example 1 | 41,000 | 321,000 | 7.83 | 0.172 | 2.03 |

Comparative Example 1

By means of the same method as in Example 1, a polymer was prepared by using a monomer in which sulfonic acid was disposed at the meta position based on a disulfonamide (—$SO_2NHSO_2$—) linker. An electrolyte membrane was manufactured by using the polymer, and the results of measuring the cation conductivity and ion exchange capacity (IEC) of the pure film are shown in the following Table 2.

TABLE 2

| Multi acid membrane | Ion conductivity (S/m) | IEC |
|---|---|---|
| Example 1 | 0.172 | 2.03 |
| Comparative Example 1 | 0.131 | 2.02 |

From the results of Table 2, it can be seen that the cation conductivity of a pure film using a polymer in which sulfonic acid in a benzene ring was disposed at the para position based on the disulfonamide (—$SO_2NHSO_2$—) linker is, under the same conditions, much higher than the cation conductivity of a pure film using a polymer in which sulfonic acid in a benzene ring was disposed at the meta position based on the disulfonamide (—$SO_2NHSO_2$—) linker, and accordingly, the performance of the electrolyte membrane is improved.

The invention claimed is:

1. A compound comprising an aromatic ring represented by the following Chemical Formula 1:

[Chemical Formula 1]

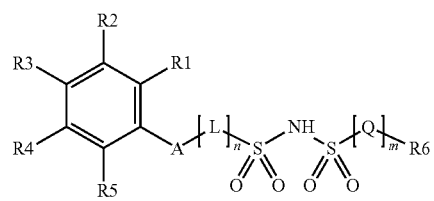

in Chemical Formula 1,

A is a direct bond, S, O, NH, or SO$_2$,

L and Q are the same as or different from each other, and are each independently represented by the following Chemical Formula 2 or 3,

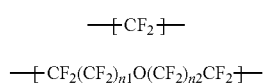
[Chemical Formula 2]

$$-\!\!+\!\!CF_2(CF_2)_{n1}O(CF_2)_{n2}CF_2\!\!+\!\!-$$
[Chemical Formula 3]

n is an integer from 1 to 16, m, n1, and n2 are each an integer from 0 to 16, when n and m are each an integer of 2 or more, a plurality of structures in the parenthesis is the same as or different from each other, two to four of R1 to R5 are the same as or different from each other, and are each independently a hydroxy group or a halogen group, and the remaining of R1 to R5 is/are hydrogen, R6 is selected from the group consisting of —SO$_3$H, —SO$_3^-$M$^+$, —COOH, —COO$^-$M$^+$, —PO$_3$H$_2$, —PO$_3$H$^-$M$^+$, -PO$_3^{2-}$2M$^+$, and a group represented by the following Chemical Formula 4,

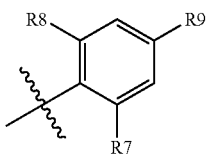
[Chemical Formula 4]

in Chemical Formula 4, at least one of R7 to R9 is selected from the group consisting of —SO$_3$H, —SO$_3^-$M$^+$, —COOH, —COO$^-$M$^+$, —PO$_3$H$_2$, —PO$_3$H$^-$M$^+$, and —PO$_3^{2-}$2M$^+$, and the others remaining of R7 to R9 are hydrogen, and M is a Group 1 element.

2. The compound of claim 1, wherein R1 and R5 are a halogen group, and R2 to R4 are hydrogen.

3. The compound of claim 1, wherein R2 and R5 are a halogen group, and R1, R3, and R4 are hydrogen.

4. The compound of claim 1, wherein R3 and R5 are a halogen group, and R1, R2, and R4 are hydrogen.

5. The compound of claim 1, wherein R2 and R4 are a halogen group or a hydroxy group, and R1, R3, and R5 are hydrogen.

6. The compound of claim 1, wherein at least one of R7 to R9 is —SO$_3$H or —SO$_3^-$M$^+$, the remaining of R7 to R9 are hydrogen, and the definition of M is the same as that in Chemical Formula 1.

7. The compound of claim 1, wherein the compound represented by Chemical Formula 1 is any one selected from the following structures:

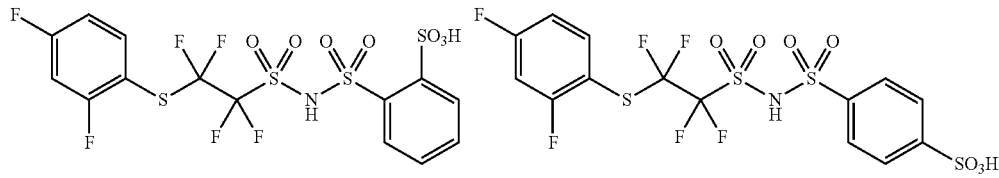

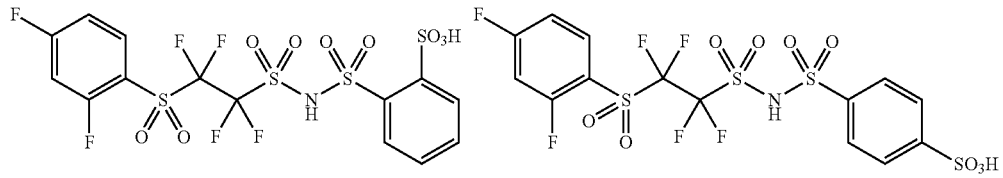

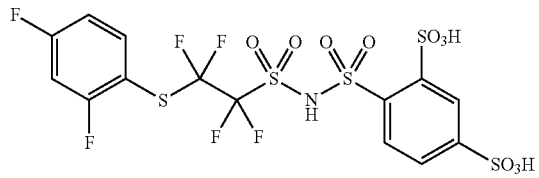

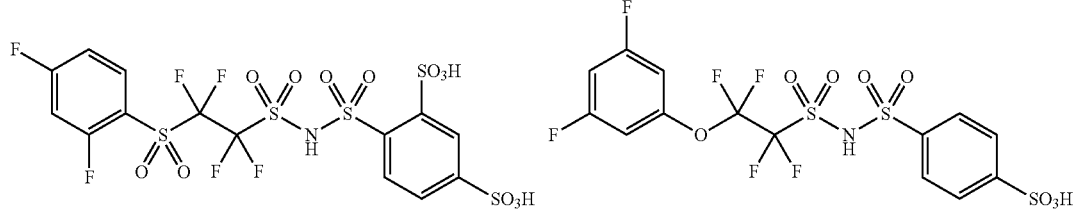

-continued
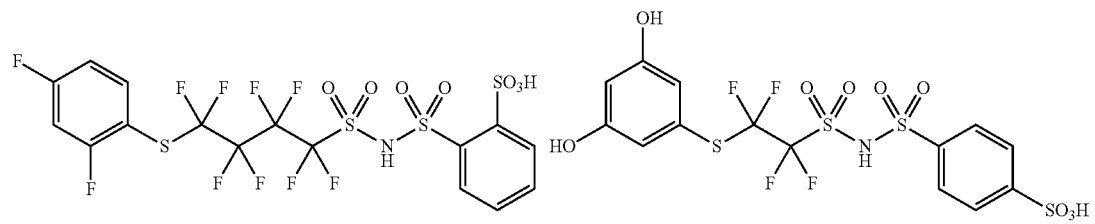
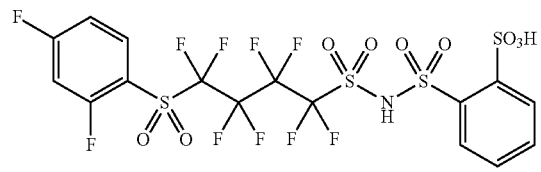
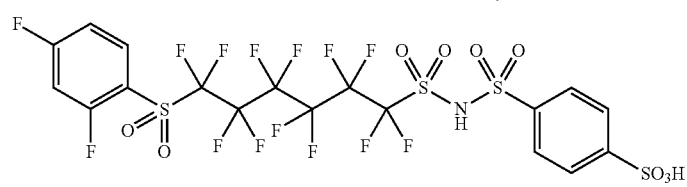
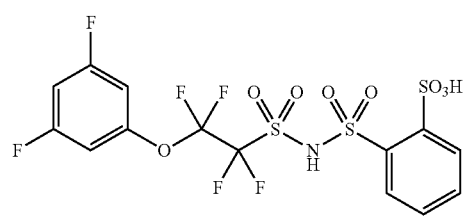
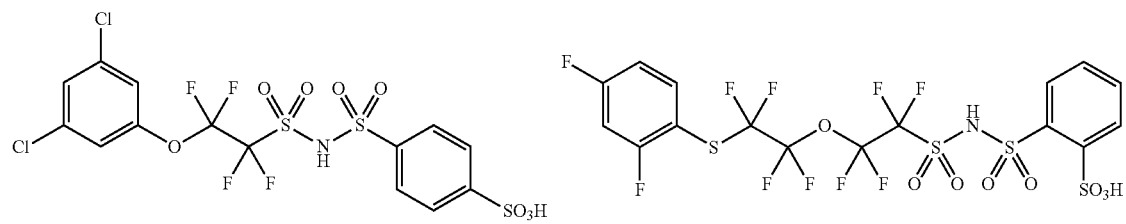
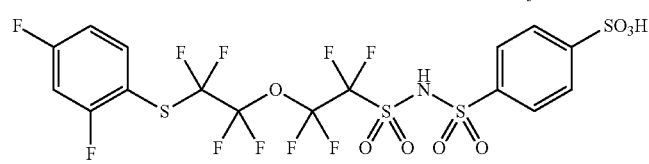
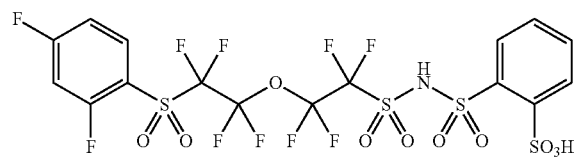
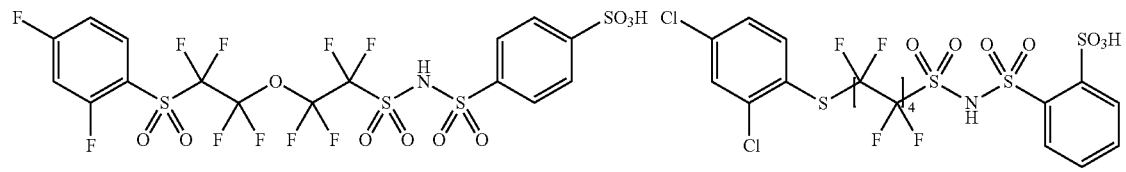
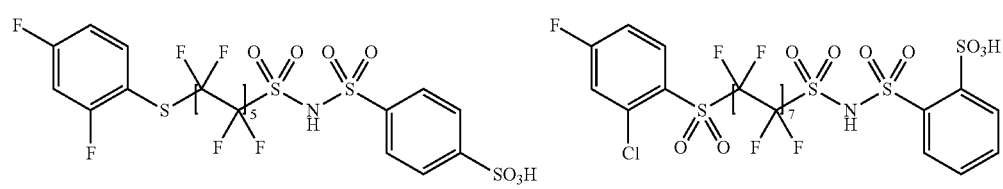

-continued
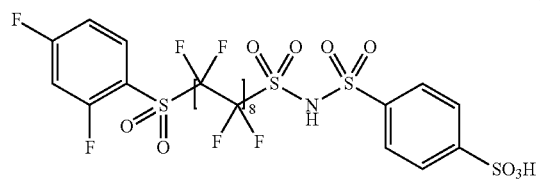
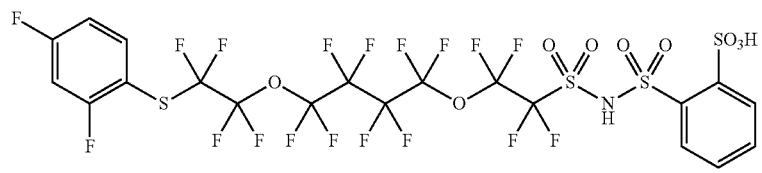
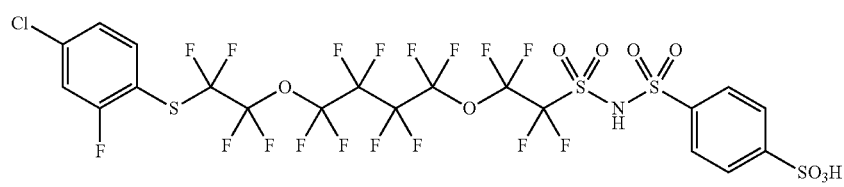
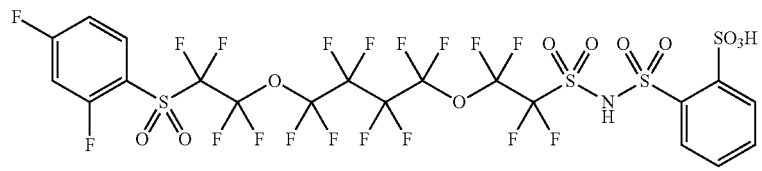
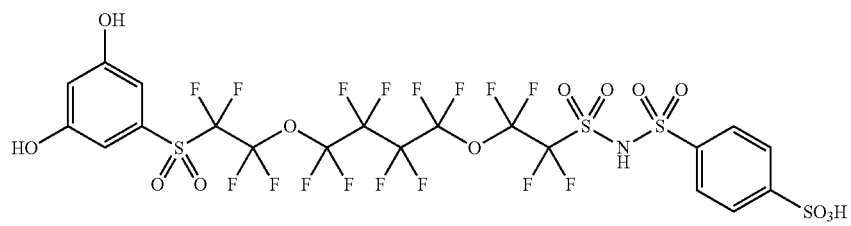
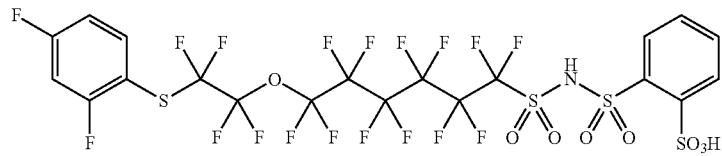
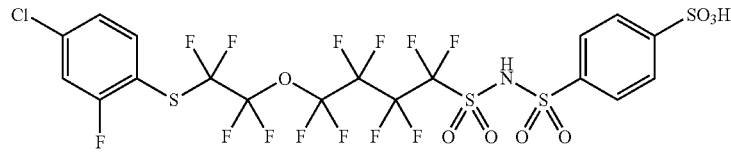
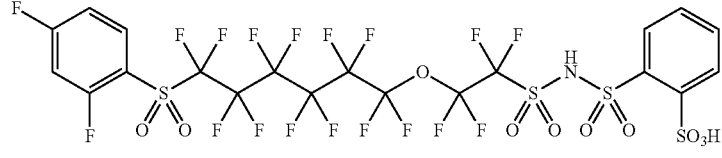
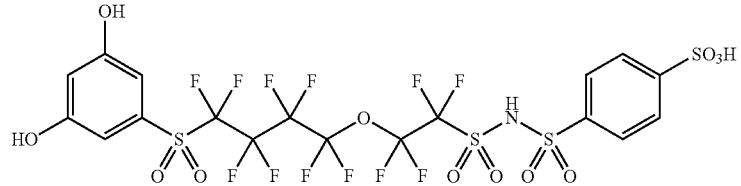

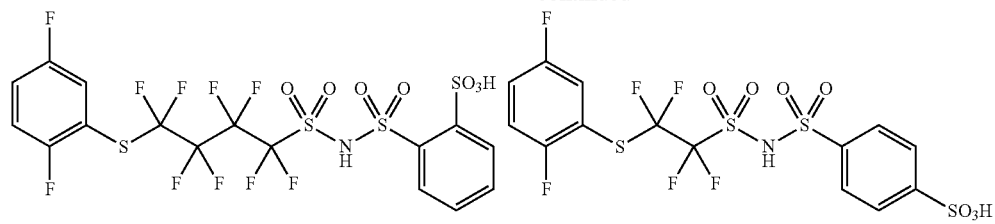
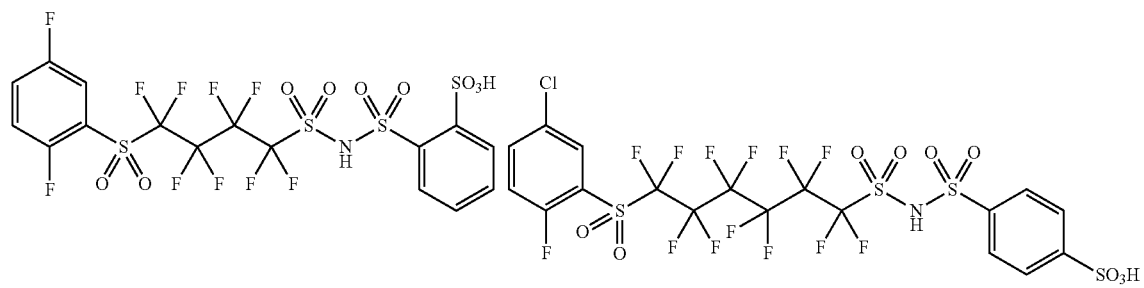
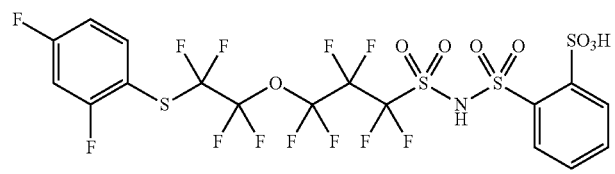
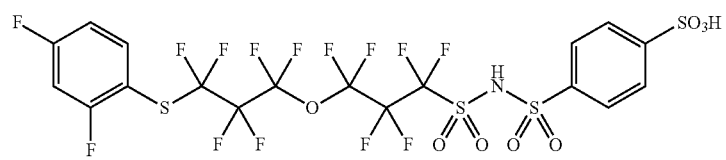
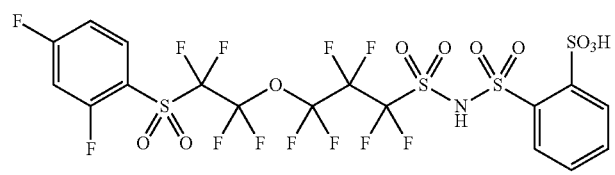
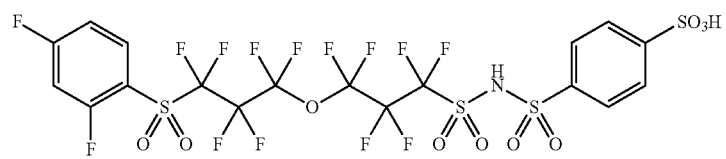
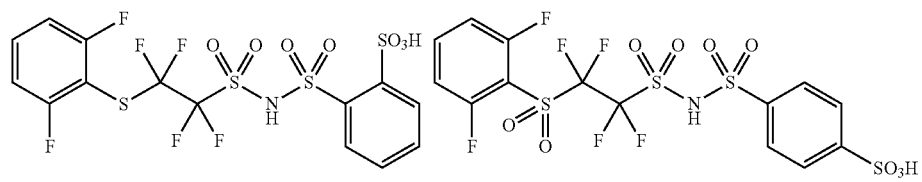

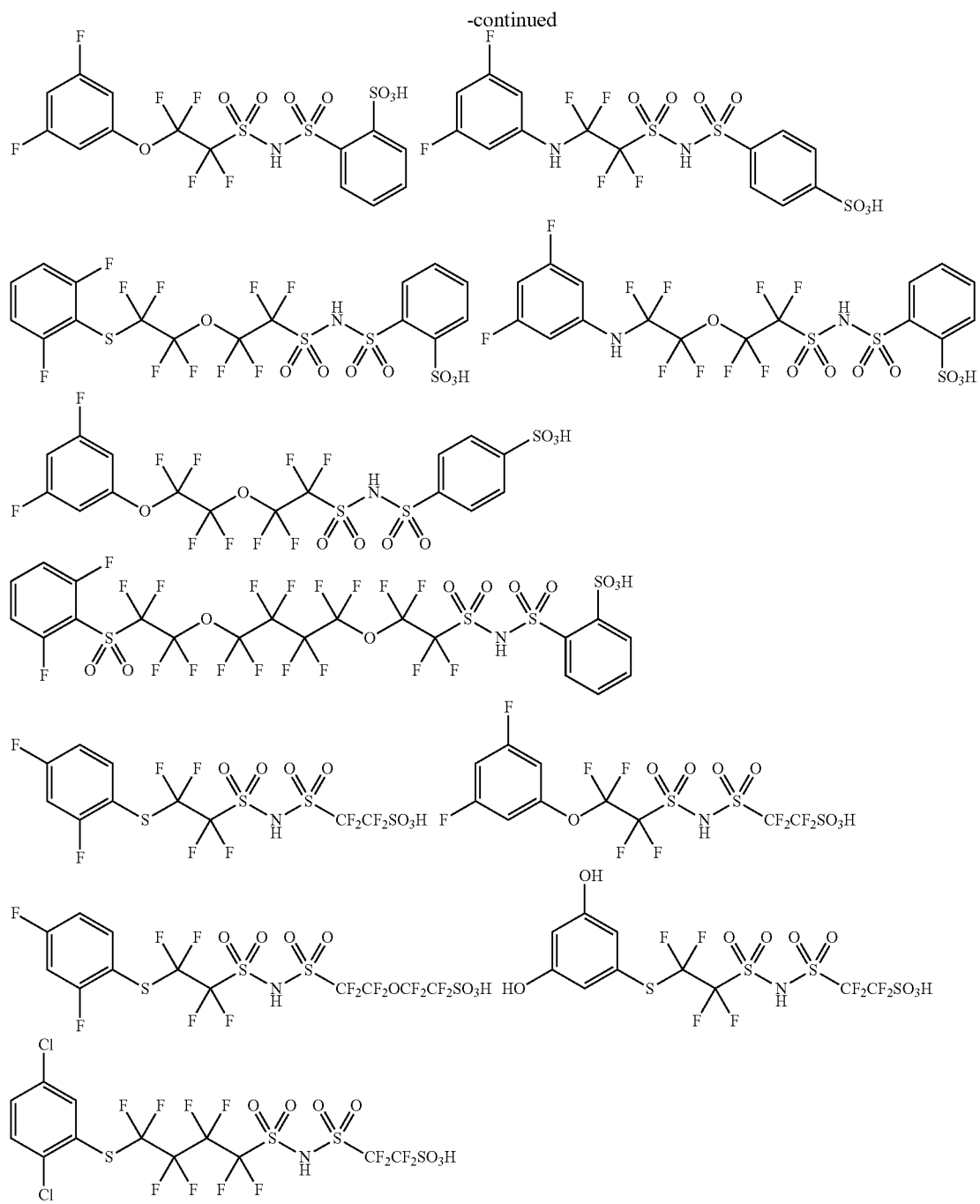
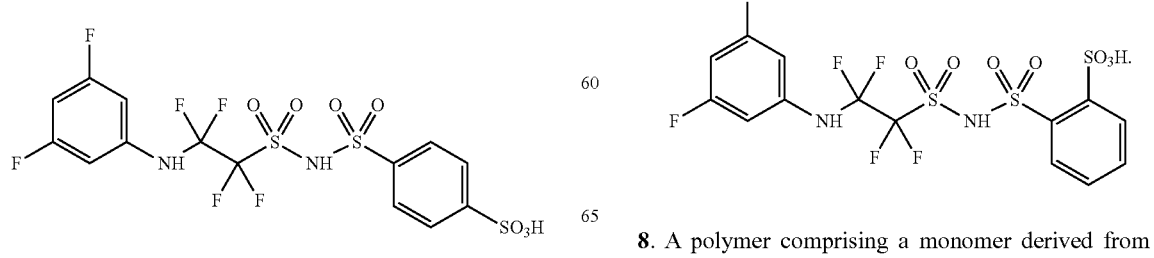
8. A polymer comprising a monomer derived from the compound of claim 1.

9. The polymer of claim 8, wherein the polymer is represented by the following Chemical Formula 5:

[Chemical Formula 5]

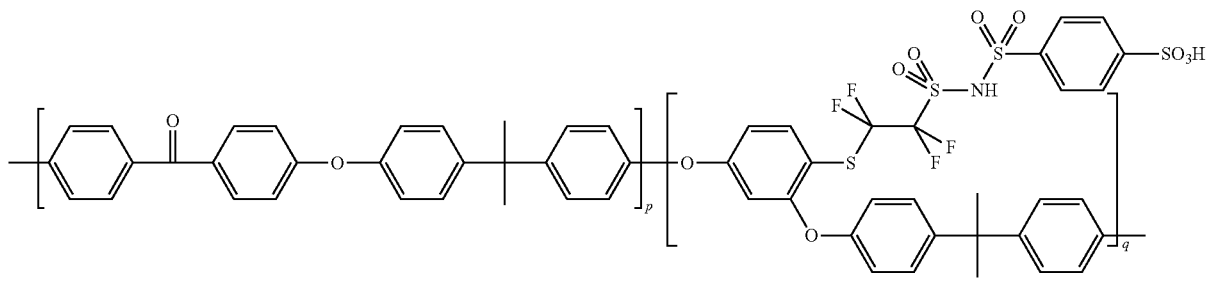

in Chemical Formula 5, p and q are each more than 0 and less than 1, and p+q=1.

10. A polyelectrolyte membrane comprising the polymer of claim 8.

11. The polyelectrolyte membrane of claim 10, wherein the polyelectrolyte membrane has an ion exchange capacity (IEC) value of 0.01 mmol/g to 7 mmol/g.

12. The polyelectrolyte membrane of claim 10, wherein the polymer has a weight average molecular weight of 500 or more and 5,000,000 or less (g/mol).

13. The polyelectrolyte membrane of claim 10, wherein the polyelectrolyte membrane has a thickness of 1 μm or more and 500 μm or less.

14. The polyelectrolyte membrane of claim 10, wherein the polyelectrolyte membrane has ion conductivity of 0.01 S/cm or more and 0.5 S/cm or less.

15. A membrane-electrode assembly comprising:

an anode;

a cathode; and the polyelectrolyte membrane of claim 10 disposed between the anode and the cathode.

16. A polyelectrolyte-type fuel cell comprising:

the two or more membrane-electrode assemblies according to claim 15;

a stack which comprises a bipolar plate disposed between the membrane-electrode assemblies;

a fuel supplying part which supplies fuel to the stack; and an oxidizing agent supplying part which supplies an oxidizing agent to the stack.

17. A redox flow battery comprising:

a positive electrode cell comprising a positive electrode and a positive electrode electrolytic solution;

a negative electrode cell comprising a negative electrode and a negative electrode electrolytic solution; and the polyelectrolyte membrane of claim 10 disposed between the positive electrode cell and the negative electrode cell.

\* \* \* \* \*